US006482978B2

(12) United States Patent
Takahashi et al.

(10) Patent No.: US 6,482,978 B2
(45) Date of Patent: Nov. 19, 2002

(54) PRODUCTION METHOD OF AROMATIC CARBOXYLIC ACID DERIVATIVE

(75) Inventors: Daisuke Takahashi, Kawasaki (JP); Masakazu Nakazawa, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/820,009

(22) Filed: Mar. 29, 2001

(65) Prior Publication Data
US 2002/0010358 A1 Jan. 24, 2002

(30) Foreign Application Priority Data

Mar. 30, 2000 (JP) ........................................ 2000-095571

(51) Int. Cl.[7] ..................... C07C 321/00; C07C 323/00; C07C 325/00; C07C 335/00; C07C 381/00
(52) U.S. Cl. ........................................ 562/426; 562/405
(58) Field of Search ................................. 562/426, 405

(56) References Cited

U.S. PATENT DOCUMENTS 5,508,272 A    4/1996   Robl

FOREIGN PATENT DOCUMENTS

| EP | 0 524 553 A1 | 1/1993 |
| EP | 0 629 627 A2 | 12/1994 |
| EP | 0 657 453 A1 | 6/1995 |
| EP | 0 747 392 A1 | 12/1996 |
| JP | 7-048259 | 2/1995 |
| JP | 8-337527 | 12/1996 |
| JP | 2000-309557 | 11/2000 |
| WO | WO-99/42431 * | 1/1999 |
| WO | WO 99/42431 | 8/1999 |
| WO | WO 99/42438 | 8/1999 |
| WO | WO 01/58865 A1 | 8/2001 |

OTHER PUBLICATIONS

Fournier–Zaluski et al, Journal of Medicinal Chemistry, 1996, 39, pp2594–2608.*
Coric et al, Journal of Medicinal Chemistry, 1996, 39, 1210–1219.*
Coric et al, Journal of Medicinal Chemistry, 1996, 39, 1210–1219; Fournier–Zaluski et al, Journal of Medicinal Chemistry, 39, 2594–2608.*
Skiles et al, Journal of medicinal Chemistry, 1986, 29, 784–796.*
Alpegiani et al, Bioorganic and Medicinal Chemistry Letters, vol. 5, No. 7, pp691–694, 1995.*

Andrew Spaltenstein, et al., "Synthesis of $C_2$–Symmetric HIV–Protease Inhibitors With Sulfur–Containing Central Units", Tetrahedron Letters, vol. 34, No. 9, pp. 1457–1460, 1993.
Marie–Claude Fournie–Zaluski, et al., "Design of Orally Active Dual Inhibitors of Neutral Endopeptidase and Angiotensin–Converting Enzyme with Long Duration of Action", Journal of Medicinal Chemistry. vol. 39, No. 13, pp. 2594–2608, 1996.
Beat Ernst, et al., "Investigation of the Chemo– and Stereoselectivity of the Ketene–Claisen Rearrangement", Helvetica Chimica Acta, vol. 80, pp. 876–891, 1997.
Aleksey V. Rukavishnikov, et al., "A tower–shaped prototypic molecule designed as an atomically sharp tip for AFM applications", Tetrahedron Letters, vol. 40, pp. 6353–6356, 1999.
Marco Alpegiani, et al., "Tricyclic Cephems as Inhibitors of Human Leukocyte Elastase Thieno[3,4–c]Cepham Sulfones and Pyrrolo[3,4–c]Cepham Sulfones", Bioorganic & Medicinal Chemistry Letters, vol. 5, No. 7, pp. 691–694, 1995.
Jerry W. Skiles, et al. "Angiotensin–Converting Enzyme Inhibitors: New Orally Active1,4–Thiazepine–2,5–diones, 1,4–Thiazine–2,5–diones, and 1,4–Benzothiazepine–2,5–diones Possessing Antihypertensive Activity", Journal of Medicinal Chemistry, vol. 29, No. 5, pp. 784–796, 1986.
P. Coric, et al., J. Med. Chem., vol. 39, No. 6, pp. 1210–1219, "Optimal Recognition of Neutral Endopeptidase and Angiotensin–Converting Enzyme Active Sites by Mercaptoacyldipeptides as a Means to Design Potent Dual Inhibitors," 1996.
Fournie–Zaluski et al, *Eur. J. Biochem.*, vol. 139, No. 2, pp. 267–274 (1984).
Coric et al., *J. Med. Chem.*, vol. 39, No. 6, pp. 1210–1219 (1996).

* cited by examiner

*Primary Examiner*—Alan L. Rotman
*Assistant Examiner*—Hector M Reyes
(74) *Attorney, Agent, or Firm*—Oblon, Spivak, McClelland, Maier & Neustadt, P.C.

(57) ABSTRACT

The present invention provides methods for producing a highly pure aromatic bromocarboxylic acid derivative and an aromatic acylthiocarboxylic acid derivative in high yields. The methods of the present invention include reacting an aromatic amino acid in an aqueous solvent in the presence of sodium nitrite, hydrogen bromide and at least one member selected from the group consisting of an aliphatic carboxylic acid and an alcohol, to give an aromatic bromocarboxylic acid derivative, and reacting the aromatic bromocarboxylic acid derivative and an organic thio acid in the presence of an amine to give an aromatic acylthiocarboxylic acid derivative.

15 Claims, No Drawings

PRODUCTION METHOD OF AROMATIC CARBOXYLIC ACID DERIVATIVE

TECHNICAL FIELD OF THE INVENTION

The present invention relates to production methods of a specific aromatic bromocarboxylic acid derivative and a specific aromatic acylthiocarboxylic acid derivative.

BACKGROUND OF THE INVENTION

Optically active aromatic acylthiocarboxylic acid derivatives are useful as pharmaceutical intermediates. For example, (S)-2-acetylthio-3-phenylpropionic acid (hereinafter sometimes to be abbreviated as (S)-ATPPA), (R)-2-bromo-3-phenylpropionic acid (hereinafter sometimes to be abbreviated as (R)-BPPA) and the like are known to be important intermediates for the compounds having an angiotensin converting enzyme inhibitory activity and a neutral endopeptidase inhibitory activity, and useful as antihypertensive agents [see particularly JP-A-7-48259 (EP-A-0629627)]. The aromatic acylthiocarboxylic acid derivatives can be produced from aromatic amino acid via aromatic bromocarboxylic acid derivatives.

For example, JP-A-8-337527 (EP-A-0747392) and JP-A-7-48259 (EP-A-0629627) disclose the following production method of (S)-ATPPA.

D-Phenylalanine is reacted with potassium bromide and sodium nitrite in a 2.5N sulfuric acid solution and amino group is substituted by bromine atom to give (R)-BPPA. The obtained (R)-BPPA is reacted with a mixture of thioacetic acid and potassium hydroxide in acetonitrile, and bromine atom is substituted by acetylthio group to give crude (S)-ATPPA. The obtained (S)-ATPPA is converted to a dicyclohexylamine (DCHA) salt, which is then recrystallized from ethyl acetate and desalted.

Further, EP-A-0524553 discloses the following production method.

D-Phenylalanine is reacted with hydrogen bromide and sodium nitrite in an aqueous solution to give (R)-BPPA. An aqueous solution of thioacetic acid and potassium carbonate is added to a sodium hydroxide solution of (R)-BPPA and the mixture is extracted with ethyl acetate. The solvent is distilled away to give (S)-ATPPA as an oil.

In addition, for example, Tetrahedron Letters, Vol. 34, p. 1457 (1993) discloses a method comprising reacting (R)- or (S)-phenylalanine with hydrogen bromide, sodium bromide and sodium nitrite to give (R)- or (S)-BPPA, and reacting the resulting compound with potassium thioacetate in methanol to give (S)- or (R)-ATPPA.

WO99/42431 discloses a method comprising reacting D-phenylalanine with hydrogen bromide and sodium nitrite in a mixed solvent of toluene and water to give (R)-BPPA.

According to the finding of the present inventors, the above-mentioned conventional methods are associated with by-production of highly hydrophobic impurities during bromination and conversion to acylthio compound. These impurities cannot be removed and have been further found to cause lower purity of crystals, markedly low yield of crystallization, an oil or oil-mixed crystals due to the inhibition of crystallization, thus exerting a profound influence on the properties of crystals, quality of crystals, crystallization yield and the like.

According to the finding of the present inventors, moreover, these impurities can be removed by once crystallizing (S)-ATPPA as a dicyclohexylamine (DCHA) salt, desalting the same and crystallizing (S)-ATPPA. However, this method requires complicated steps and is economically disadvantageous, combined with lower yields.

SUMMARY OF THE INVENTION

It is therefore and object of the present invention to provide a superior production method of an aromatic bromocarboxylic acid derivative, such as (R)-BPPA and the like, and an aromatic acylthiocarboxylic acid derivative, such as (S)-ATPPA and the like, at a high purity and in a high yield.

According to the present invention, it has been found that generation of highly hydrophobic impurities during bromination can be dramatically suppressed by reacting an aromatic amino acid in an aqueous solvent in the presence of sodium nitrite, hydrogen bromide, and at least one member selected from the group consisting of an aliphatic carboxylic acid and an alcohol to produce an aromatic bromocarboxylic acid derivative. It has been also found that generation of highly hydrophobic impurities during conversion to acylthio compound can be dramatically suppressed by reacting an aromatic bromocarboxylic acid derivative and an organic thio acid in the presence of an amine to produce an aromatic acylthiocarboxylic acid derivative.

The present inventors have completed the present invention based on the above-mentioned findings.

Accordingly, the present invention provides the following.

A method for producing an aromatic acylthiocarboxylic acid derivative of the formula (3)

(3)

wherein A is an optionally substituted aryl having 6 to 15 carbon atoms, an optionally substituted aralkyl having 7 to 20 carbon atoms or a group having a carbon skeleton of said aryl or aralkyl, which comprises a heteroatom in the skeleton, and R is an alkyl having 1 to 6 carbon atoms, an aryl having 6 to 10 carbon atoms or an aralkyl having 7 to 11 carbon atoms, which method comprises reacting an aromatic amino acid of the following formula (1)

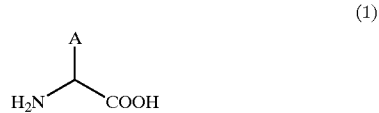

(1)

wherein A is as defined above, in an aqueous solvent in the presence of sodium nitrite, hydrogen bromide and at least one member selected from the group consisting of an aliphatic carboxylic acid and an alcohol, to produce an aromatic bromocarboxylic acid derivative of the formula (2)

(2)

wherein A is as defined above, and reacting the aromatic bromocarboxylic acid derivative and an organic thio acid in the presence of an amine.

The present invention also provides a method for producing an aromatic bromocarboxylic acid derivative of the formula (2), which comprises reacting an aromatic amino acid of the formula (1) in an aqueous solvent in the presence of sodium nitrite, hydrogen bromide and at least one member selected from the group consisting of an aliphatic carboxylic acid and an alcohol.

The present invention further provides a method for producing an aromatic acylthiocarboxylic acid derivative of the formula (3), which comprises reacting an aromatic bromocarboxylic acid derivative of the formula (2) and an organic thio acid in the presence of an amine.

DETAILED DESCRIPTION OF THE INVENTION

The present invention is explained in detail in the following.

In the formulas in the present invention, A means optionally substituted aryl having 6 to 15 carbon atoms, optionally substituted aralkyl having 7 to 20 carbon atoms or a group having a carbon skeleton of said aryl or aralkyl and comprising a heteroatom in the skeleton. When A has one or more substituent(s), the substituent is not subject to any particular limitation as long as it does not adversely affect the reaction in the present invention. Examples thereof include alkoxy (preferably that having 1 to 7 carbon atoms), nitro, alkyl (preferably that having 1 to 6 carbon atoms), aralkyl (preferably that having 7 to 11 carbon atoms), halogen atoms, hydroxyl having protecting group, carboxyl, amino having protecting group and the like.

The group containing a heteroatom (e.g., nitrogen, oxygen, sulfur atoms and the like) in the carbon skeleton is, for example, (p-methylbenzyl)thiomethyl, (p-methoxybenzyl)thiomethyl, benzyloxymethyl, benzyloxyethyl, 4-(t-butoxy)phenylmethyl, 4-benzyloxyphenylmethyl, phenylthiomethyl and the like.

A may be a group introduced using aromatic amino acid having a protected side chain functional group, such as O-benzyltyrosine and the like, as a starting material.

A is particularly preferably benzyl.

In the formulas in the present invention, R is alkyl having 1 to 6 carbon atoms, aryl having 6 to 10 carbon atoms or aralkyl having 7 to 11 carbon atoms. Examples of alkyl having 1 to 6 carbon atoms preferably include methyl, ethyl, butyl, t-butyl, isopropyl and the like. Examples of aryl having 6 to 10 carbon atoms preferably include phenyl, naphthyl and the like. Examples of aralkyl having 7 to 11 carbon atoms preferably include benzyl and the like. Examples of R preferably include methyl and benzyl, particularly preferably methyl.

Representative compounds preferably produced by the production method of the present invention may be, for example, the aforementioned (R)-BPPA and (S)-ATPPA derived from D-phenylalanine.

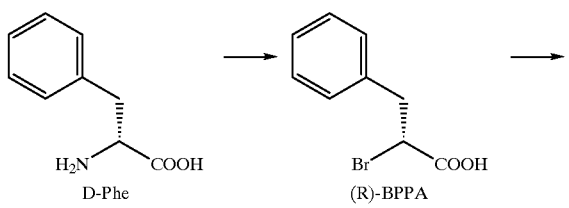

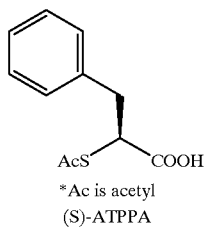

*Ac is acetyl
(S)-ATPPA

The method for producing an aromatic bromocarboxylic acid derivative of the aforementioned formula (2) is explained in the following.

The aromatic bromocarboxylic acid derivative of the aforementioned formula (2) can be produced by reacting the aromatic amino acid of the aforementioned formula (1) in an aqueous solvent in the presence of sodium nitrite, hydrogen bromide and at least one member selected from the group consisting of an aliphatic carboxylic acid and an alcohol.

For example, sodium nitrite is added (preferably added dropwise) to a mixture of an aqueous solvent, an aromatic amino acid, aqueous hydrogen bromide and an alcohol (and/or an aliphatic carboxylic acid) to allow reaction. A different solvent may be optionally added as long as the effect of the present invention is not inhibited.

The reaction temperature is not subject to any particular limitation, but it is generally −10° C. to 40° C., preferably −5° C. to 20° C. The reaction time is not subject to any particular limitation, but it is generally not less than 1 hour, preferably 3–8 hours.

The amount added of sodium nitrite is generally 1–3 molar equivalents, preferably 1.1–2 molar equivalents, per 1 molar equivalent of the starting material, aromatic amino acid. Similarly, hydrogen bromide is used in an amount of generally 1–8 molar equivalents, preferably 2–5 molar equivalents, per 1 molar equivalent of the starting material, aromatic amino acid.

As shown in Tetrahedron Letters, Vol. 34, p. 1457 (1993) and the like, sodium bromide, potassium bromide and the like may be present during the reaction. When sodium bromide, potassium bromide and the like are to be present, the amount thereof to be used is 0.1–3 molar equivalents, preferably 0.5–1.5 molar equivalents, per 1 molar equivalent of the starting material, aromatic amino acid.

The aliphatic carboxylic acid in the present invention may be substituted with a halogen atom such as fluoro atom. For example, acetic acid, formic acid, trifluoroacetic acid, propionic acid, butanoic acid and the like are preferable. More preferably, acetic acid, formic acid and propionic acid are used, and particularly preferably, acetic acid is used.

Examples of alcohol in the present invention preferably include lower alcohol having 1 to 6 carbon atoms such as methanol, ethanol, 1-propanol, 2-propanol, butanol and the like. More preferably, alcohol having 3 or 4 carbon atoms, such as 1-propanol, 2-propanol, butanol and the like, is used, and particularly preferably, 2-propanol is used.

In the present invention, both or either one of aliphatic carboxylic acid and alcohol may be used, where alcohol is preferred to aliphatic carboxylic acid.

The amount of alcohol or aliphatic carboxylic acid contained in the aqueous solvent is not subject to any particular limitation, but it is generally 0.1 to 20-fold amount (wt/wt), preferably 0.5 to 5-fold amount (wt/wt), relative to the amount of aromatic amino acid.

As the aforementioned aqueous solvent, water is preferable. As long as the effect of the present invention is not impaired, a mixed solvent of an organic solvent (e.g., acetonitrile, tetrahydrofuran and the like) and water can be used. The amount of the aqueous solvent is not subject to any particular limitation, but it is generally 1 to 50-fold amount (wt/wt) relative to the amount of aromatic amino acid.

After the completion of the reaction, the reaction mixture is concentrated or the solvent is distilled away as necessary, and the residue is extracted with a solvent such as toluene, ethyl acetate, isopropyl alcohol, methyl isobutyl ketone, methyl t-butyl ether and the like. Thereafter, the extract solvent is distilled away to give an aromatic bromocarboxylic acid derivative. It is also possible to convert the aromatic bromocarboxylic acid derivative to a salt, such as an amine salt and the like, and obtain the salt as a solid or crystals by crystallization and the like.

By the above-mentioned method, the production of highly hydrophobic impurities during the step of producing an aromatic bromocarboxylic acid derivative from aromatic amino acid can be strikingly inhibited, whereby a highly pure aromatic bromocarboxylic acid derivative is obtained.

A method for producing an aromatic acylthiocarboxylic acid derivative of the aforementioned formula (3) is explained in the following.

An aromatic bromocarboxylic acid derivative of the aforementioned formula (2) and an organic thio acid are reacted in the presence of an amine to give an aromatic acylthiocarboxylic acid derivative of the aforementioned formula (3). For example, an organic thio acid, an amine and an aromatic bromocarboxylic acid derivative are added to a solvent to allow reaction. The order of the addition of these components is not subject to any particular limitation. It is also possible to convert the aromatic bromocarboxylic acid derivative to an amine salt in advance, and further add an amine as necessary to allow reaction with an organic thio acid in a solvent.

The organic thio acid is represented by the following formula (4)

R—COSH           (4)

wherein R is as defined above.

Examples thereof include thioacetic acid, thiobenzoic acid, thiopropionic acid and the like, with preference given to thioacetic acid and thiobenzoic acid, and particular preference given to thioacetic acid.

The reaction temperature is not subject to any particular limitation, but it is generally −10° C. to 40° C., preferably 5° C. to 25° C. The reaction time is not subject to any particular limitation, but it is generally not shorter than 0.5 hour. The reaction time is preferably 1–5 hours.

The amount of organic thio acid is generally 0.8 molar equivalent—3.0 molar equivalents, preferably 1.0 molar equivalent—2.0 molar equivalents, per 1 molar equivalent of aromatic bromocarboxylic acid derivative.

The amount of amine to be used is not subject to any particular limitation. To increase the reaction yield, generally 1 molar equivalent or more of amine is used per 1 molar equivalent of aromatic bromocarboxylic acid derivative. Preferably, 1 molar equivalent—2 molar equivalents, more preferably 1.3 molar equivalents—1.6 molar equivalents, of amine is used.

When amine is one having plural amino groups in one molecule, such as ethylenediamine and the like, it is used in an amount equivalent to that obtained by dividing the above-mentioned amount by the number of amino groups.

It is also possible to concurrently use a base other than amine in the above-mentioned amount. However, it is generally unnecessary because impurities are produced when the amount of amine is insufficient.

The solvent to be used in this step is, for example, acetates such as ethyl acetate, isopropyl acetate, butyl acetate and the like, alcohols such as methanol, ethanol, isopropyl alcohol, butanol and the like, ethers such as diethyl ether, methyl t-butyl ether and the like, ketones such as acetone, methyl isobutyl ketone and the like, hydrocarbons such as cyclohexane, toluene, benzene and the like, halogenated hydrocarbons such as dichloromethane, dichloroethane and the like, dimethylformamide, water, a mixed solvent of optional solvents from these and the like. Preferably, it is exemplified by ethyl acetate, isopropyl alcohol, ethanol, methanol, methyl isobutyl ketone and toluene.

Preferable examples of amine include triethylamine, diethylamine, isobutylamine, diisopropylamine, dicyclohexylamine, cyclohexylamine, diisopropylethylamine, ethylenediamine, dimethylaminopyridine and the like.

The amine is more preferably triethylamine, diethylamine, diisopropylamine, dicyclohexylamine and the like, particularly preferably triethylamine.

By the above-mentioned method, the production of highly hydrophobic impurities in a step to produce an aromatic acylthiocarboxylic acid derivative from an aromatic bromocarboxylic acid derivative can be strikingly inhibited. When the aforementioned production method of the aromatic bromocarboxylic acid derivative of the present invention is combined, a highly pure aromatic acylthiocarboxylic acid derivative can be obtained.

The aromatic acylthiocarboxylic acid obtained according to the production method of the present invention has a dramatically reduced content of highly hydrophobic impurities that cause various problems in a crystallization step. Consequently, highly pure aromatic acylthiocarboxylic acid crystals can be obtained in high yields by crystallization.

Preferable solvents to be used for crystallization include hydrocarbon solvents such as cyclohexane, heptane, hexane, methylcyclohexane and the like. A mixed solvent of these hydrocarbon solvents and different solvents can be used as long as it does not influence the crystallization yield and the like. Examples of the different solvents include acetates such as ethyl acetate and the like, alcohols such as methanol, ethanol, propyl alcohol, butanol and the like, ethers such as diethyl ether, methyl t-butyl ether and the like, ketones such as acetone, methyl isobutyl ketone and the like, halogenated hydrocarbons such as dichloromethane, dichloroethane and the like, aromatic hydrocarbon solvent such as toluene, benzene and the like, dimethylformamide and the like.

The method for crystallization is not subject to any particular limitation, and a method known to those of ordinary skill in the art can be used (concentration crystallization, cooling crystallization and the like), which is particularly preferably cooling crystallization.

The present invention is explained in detail by referring to the examples. The present invention is not limited by these examples in any way. The yield and impurities were analyzed by HPLC using an Inertsil® ODS-2 column (GL Sciences Inc.).

EXAMPLE 1

D-Phenylalanine (10 g, 61 mmol), acetic acid (10 ml), water (10 ml), potassium bromide (8.36 g, 70 mmol) and 48% aqueous hydrogen bromide (41 g, 243 mmol) were mixed. A 33% aqueous sodium nitrite solution (16 g, 76 mmol) was dropwise added over 2 hours under ice-cooling. The mixture was stirred for 3 hours, and then overnight at room temperature. After extraction with toluene, the organic layer was washed successively with 2% aqueous sodium sulfite solution and 20% brine, and concentrated to give (R)-BPPA as an oil. By the HPLC analysis, the yield of (R)-BPPA was 81% (11.3 g).

EXAMPLE 2

D-Phenylalanine (2 g, 12 mmol), isopropyl alcohol (8 ml), potassium bromide (1.2 g, 10 mmol) and 48% aqueous hydrogen bromide (8.3 g, 49 mmol) were mixed. A 33% aqueous sodium nitrite solution (3.0 g, 15 mmol) was dropwise added over 2 hours under ice-cooling. The mixture was stirred for 3 hours, and then overnight at room temperature. After extraction with toluene, the organic layer was washed successively with 2% aqueous sodium sulfite solution and 20% brine, and concentrated to give (R)-BPPA as an oil. By the HPLC analysis, the yield of (R)-BPPA was 82% (2.3 g).

EXAMPLE 3

The (R)-BPPA (7.8 g) obtained as an oil in Example 2 was dissolved in toluene, and thioacetic acid (4.1 g) was added under ice-cooling, which was followed by dropwise addition of triethylamine (4.9 g). After stirring for 3 hr, the mixture was washed twice with 3% aqueous potassium hydrogensulfate solution and concentrated to dryness to give (S)-ATPPA (7.5 g, yield 98%).

Cyclohexane (45 ml) was added to the obtained (S)-ATPPA (5.8 g) and the mixture was heated to 50° C. for dissolution. Thereafter, the crystal seed was inoculated and the mixture was subjected to cooling crystallization to give (S)-ATPPA as crystals (yield 4.9 g, crystallization yield 85%).

COMPARATIVE EXAMPLE 1

D-Phenylalanine (10 g, 61 mmol), water (25 ml), potassium bromide (8.36 g, 70 mmol) and 48% aqueous hydrogen bromide (41 g, 243 mmol) were mixed. A 33% aqueous sodium nitrite solution (16 g, 76 mmol) was dropwise added over 2 hours under ice-cooling. The mixture was stirred for 3 hours, and at room temperature overnight. After extraction with toluene, the organic layer was washed successively with 2% aqueous sodium sulfite solution and 20% brine, and concentrated to give (R)-BPPA as an oil. By the HPLC analysis, the yield of (R)-BPPA was 74% (10.3 g).

COMPARATIVE EXAMPLE 2

The (R)-BPPA (10 g) obtained as an oil in Comparative Example 1 was dissolved in methyl isobutyl ketone, and gradually added dropwise to a suspension of potassium thioacetate (7.3 g) in methyl isobutyl ketone. After stirring overnight, the mixture was washed twice with 3% aqueous potassium hydrogensulfate solution, washed with 20% brine and concentrated to dryness to give (S)-ATPPA (9.8 g, yield 98%) as an oil.

Cyclohexane (35 ml) was added to the obtained (S)-ATPPA (6.8 g) and the mixture was heated to 50° C. for dissolution. Thereafter, the crystal seed was inoculated and the mixture was subjected to cooling crystallization to give (S)-ATPPA as crystals (yield 5.3 g, crystallization yield 79%).

COMPARATIVE EXAMPLE 3

D-Phenylalanine (10 g, 61 mmol), water (15 ml), toluene (17 ml), potassium bromide (3.6 g, 31 mmol) and 48% aqueous hydrogen bromide (40.8 g, 242 mmol) were mixed. A solution of sodium nitrite (5.43 g, 78 mmol) in water (10 ml) was dropwise added over 5 hours at −5° C. After stirring for 3 hours, the mixture was stirred at 15° C. for 8 more hours. After extraction with toluene, the organic layer was washed successively with 2% aqueous sodium sulfite solution and 20% brine, and concentrated to give (R)-BPPA as an oil. By the HPLC analysis, the yield of (R)-BPPA was 76.5% (10.6 g).

The impurity contents and crystallization yield of (S)-ATPPA crystals in Comparative Examples and Examples are summarized in the following, wherein the impurities produced in the bromination step are shown as impurity X, and those produced in the acylation step are shown as impurity Y.

TABLE 1

|  | Example 1 | Example 2 | Comparative Example 1 | Comparative Example 3 |
|---|---|---|---|---|
| Content (%) of impurity X | 1.6 | 0.4 | 4.3 | 4.3 |

TABLE 2

|  | Example 3 | Comparative Example 2 |
|---|---|---|
| Content (%) of impurity X in crystals | 0.1 | 2.9 |
| Content (%) of impurity Y in crystals | 0 | 3.6 |
| (S)-ATPPA crystallization yield (%) | 85 | 79 |

According to the present invention, the production of highly hydrophobic impurities during the production of an aromatic acylthiocarboxylic acid derivative and a precursor thereof, aromatic bromocarboxylic acid derivative, can be strikingly inhibited. Therefore, a highly pure aromatic bromocarboxylic acid derivative and a highly pure aromatic acylthiocarboxylic acid derivative, which are useful pharmaceutical intermediates, can be obtained.

This application is based on a patent application No. 95571/2000 filed in Japan, the contents of which are hereby incorporated by reference.

What is claimed is:

1. A method for producing an aromatic acylthiocarboxylic acid derivative of the formula (3)

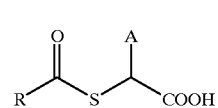

(3)

wherein A is an optionally substituted aryl having 6 to 15 carbon atoms, an optionally substituted aralkyl having 7 to 20 carbon atoms or a group having a carbon skeleton of said aryl or aralkyl and comprising a heteroatom in the skeleton, and R is an alkyl having 1 to 6 carbon atoms, an aryl having 6 to 10 carbon atoms or an aralkyl having 7 to 11 carbon atoms, which method comprises the steps of (a) reacting an aromatic amino acid of the following formula (1)

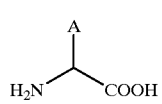

(1)

wherein A is as defined above, in an aqueous solvent in the presence of sodium nitrite, hydrogen bromide and at least one member selected from the group consisting of an aliphatic carboxylic acid and an alcohol, to produce an aromatic bromocarboxylic acid derivative of the formula (2)

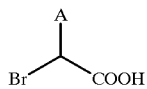

(2)

wherein a is as defined above, and (b) reacting the aromatic bromocarboxylic acid derivative and an organic thio acid in the presence of an amine.

2. The method of claim 1, wherein A is benzyl.

3. The method of claim 1, wherein the aromatic amino acid of the formula (1) is D-phenylalanine, the aromatic bromocarboxylic acid derivative of the formula (2) is (R)-2-bromo-3-phenylpropionic acid, and the aromatic acylthiocarboxylic acid derivative of the formula (3) is (S)-2-acetylthio-3-phenylpropionic acid.

4. The method of claim 1, wherein the aliphatic carboxylic acid is selected from the group consisting of acetic acid, formic acid, trifluoroacetic acid, propionic acid and butanoic acid.

5. The method of claim 1, wherein the alcohol has 1 to 6 carbon atoms.

6. The method of claim 1, wherein the amine is selected from the group consisting of triethylamine, diethylamine, isobutylamine, diisopropylamine, dicyclohexylamine, cyclohexylamine, diisopropylethylamine, ethylenediamine and dimethylaminopyridine.

7. A method for producing an aromatic bromocarboxylic acid derivative of the formula (2)

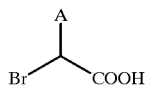

(2)

wherein A is an optionally substituted aryl having 6 to 15 carbon atoms, an optionally substituted aralkyl having 7 to 20 carbon atoms or a group having a carbon skeleton of said aryl or aralkyl and comprising a heteroatom in the skeleton, which method comprises reacting an aromatic amino acid of the formula (1)

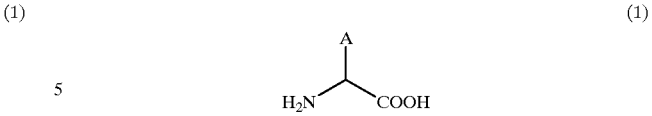

(1)

wherein A is as defined above, in an aqueous solvent in the presence of sodium nitrite, hydrogen bromide and at least one member selected from the group consisting of an aliphatic carboxylic acid and an alcohol.

8. The method of claim 7, wherein A is benzyl.

9. The method of claim 7, wherein the aromatic amino acid of the formula (1) is D-phenylalanine and the aromatic bromocarboxylic acid derivative of the formula (2) is (R)-2-bromo-3-phenylpropionic acid.

10. The method of claim 7, wherein the aliphatic carboxylic acid is selected from the group consisting of acetic acid, formic acid, trifluoroacetic acid, propionic acid and butanoic acid.

11. The method of claim 7, wherein the alcohol has 1 to 6 carbon atoms.

12. A method for producing an aromatic acylthiocarboxylic acid derivative of the formula (3)

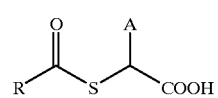

(3)

wherein A is an optionally substituted aryl having 6 to 15 carbon atoms, an optionally substituted aralkyl having 7 to 20 carbon atoms or a group having a carbon skeleton of said aryl or aralkyl and comprising a heteroatom in the skeleton, and R is an alkyl having 1 to 6 carbon atoms, an aryl having 6 to 10 carbon atoms or an aralkyl having 7 to 11 carbon atoms, which method comprises reacting an aromatic bromocarboxylic acid derivative of the formula (2)

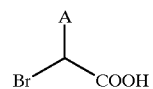

(2)

wherein A is as defined above, and an organic thio acid in the presence of an amine.

13. The method of claim 12, wherein A is benzyl.

14. The method of claim 12, wherein the aromatic bromocarboxylic acid derivative of the formula (2) is (R)-2-bromo-3-phenylpropionic acid and the aromatic acylthiocarboxylic acid derivative of the formula (3) is (S)-2-acetylthio-3-phenylpropionic acid.

15. The method of claim 12, wherein the amine is selected from the group consisting of triethylamine, diethylamine, isobutylamine, diisopropylamine, dicyclohexylamine, cyclohexylamine, diisopropylethylamine, ethylenediamine and dimethylaminopyridine.

* * * * *